United States Patent
Al-Saeedi

(10) Patent No.: US 8,314,080 B2
(45) Date of Patent: Nov. 20, 2012

(54) METHOD OF TREATING TYPE I DIABETES

(75) Inventor: Fatma Jassab Faleh Marzooq Al-Saeedi, Safat (KW)

(73) Assignee: Kuwait University, Safat (KW)

( * ) Notice: Subject to any disclaimer, the term of this patent is extended or adjusted under 35 U.S.C. 154(b) by 267 days.

(21) Appl. No.: 12/662,231

(22) Filed: Apr. 6, 2010

(65) Prior Publication Data

US 2011/0245348 A1 Oct. 6, 2011

(51) Int. Cl.
*A61K 31/685* (2006.01)

(52) U.S. Cl. .......................................... 514/78; 514/866

(58) Field of Classification Search ............... 514/78, 514/866

See application file for complete search history.

(56) References Cited

U.S. PATENT DOCUMENTS

| | | | |
|---|---|---|---|
| 3,197,368 | A | 7/1965 | Rolf et al. |
| 7,579,025 | B2 | 8/2009 | Campbell-Tofte |
| 2006/0257502 | A1 | 11/2006 | Liu |
| 2008/0146490 | A1 | 6/2008 | Joabsson et al. |

FOREIGN PATENT DOCUMENTS

| | | |
|---|---|---|
| CN | 1070827 A | 4/1993 |
| GB | 1173160 A | 12/1969 |
| JP | 2006316016 A | 11/2006 |
| WO | WO 97/16184 | 5/1997 |
| WO | WO 01/76583 A1 | 10/2001 |
| WO | WO 2005065675 A1 * | 7/2005 |
| WO | WO 2006/018294 A1 | 2/2006 |

* cited by examiner

*Primary Examiner* — Kevin E Weddington
(74) *Attorney, Agent, or Firm* — Richard C. Litman

(57) ABSTRACT

The method of treating type I diabetes includes the treatment of diabetic patients with choline in order to control the patient's lipid profile. The treatment method includes the step of administering to the patient a therapeutically effective dosage of choline or a pharmaceutically acceptable salt thereof. In human patients, the effective dosage of choline is preferably approximately 10 mg., delivered daily. Although the choline may be injected in solution, it is preferably delivered orally to the patient.

2 Claims, 2 Drawing Sheets

METHOD OF TREATING TYPE I DIABETES

BACKGROUND OF THE INVENTION

1. Field of the Invention

The present invention relates to the treatment of type I diabetes. The treatment method includes the step of administering to the patient a therapeutically effective dosage of choline.

2. Description of the Related Art

Diabetes mellitus (commonly referred to as just "diabetes") is a condition in which a person has a high blood sugar (glucose) level as a result of the body either not producing enough insulin, or because body cells do not properly respond to the insulin that is produced. Insulin is a hormone produced in the pancreas that enables body cells to absorb glucose, which is then converted into usable energy. If the body cells do not absorb the glucose, the glucose accumulates in the blood (a condition known as "hyperglycemia"), leading to various potential medical complications.

There are many types of diabetes, with the most common being Type I diabetes, which results from the body's failure to produce insulin, and presently requires the patient to inject insulin; Type II diabetes, which results from insulin resistance, a condition in which cells fail to use insulin properly, sometimes combined with an absolute insulin deficiency; and Gestational diabetes, in which pregnant women, who have never had diabetes before, have a high blood glucose level during pregnancy. Gestational diabetes may precede development of type II diabetes.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

All forms of diabetes have been treatable since insulin became medically available in 1921, but a cure is difficult. Pancreas transplants have been tried with limited success in type I diabetes; gastric bypass surgery has been successful in many with morbid obesity and type II diabetes; and gestational diabetes usually resolves after delivery. Diabetes without proper treatments can cause many complications. Acute complications include hypoglycemia, diabetic ketoacidosis, or nonketotic hyperosmolar coma. Serious long-term complications include cardiovascular disease, chronic renal failure, and retinal damage. Adequate treatment of diabetes is thus important.

Diabetes mellitus type I (also referred to as "type I diabetes", insulin deficient diabetes mellitus (IDDM), or juvenile diabetes) is a form of diabetes mellitus that results from autoimmune destruction of insulin-producing beta cells of the pancreas. The subsequent lack of insulin leads to increased blood and urine glucose. The classical symptoms of polyuria (i.e., frequent urination), polydipsia (i.e., increased thirst), polyphagia (i.e., increased hunger), and weight loss are common results of type I diabetes.

Type I diabetes is typically fatal unless treated with insulin. Injection is the most common method of administering insulin, although insulin pumps and insulin inhalers are available. Pancreas transplants have also been used to treat type I diabetes. However, this procedure is currently still at the experimental trial stage.

There is presently no preventive measure against developing type I diabetes. Most people who develop type I diabetes are otherwise healthy. Although the cause of type I diabetes is still not fully understood, it is believed to be of immunological origin. Type I diabetes can be distinguished from type II diabetes via a C-peptide assay, which measures endogenous insulin production.

Type 1 treatment must be continued indefinitely in all cases. Treatment need not significantly impair normal activities, if sufficient patient training, awareness, appropriate care, discipline in testing and dosing of insulin is taken. However, treatment is burdensome for many people. Complications may be associated with both low blood sugar and high blood sugar. Low blood sugar may lead to seizures or episodes of unconsciousness and requires emergency treatment. High blood sugar may lead to increased tiredness and can also result in long-term damage to other organs such as eyes and joints.

Thus, a method of treating type I diabetes solving the aforementioned problems is desired.

SUMMARY OF THE INVENTION

The method of treating type I diabetes includes the treatment of diabetic patients with choline in order to control the patient's lipid profile. The treatment method includes the step of administering to the patient a therapeutically effective dosage of choline or a pharmaceutically acceptable salt thereof.

In human patients, the effective dosage of choline is preferably approximately 10 mg., delivered daily. Although the choline may be injected in solution, it is preferably delivered orally to the patient.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The method of treating type I diabetes includes the treatment of diabetic patients with choline in order to control the patient's lipid profile. In the conventional treatment of type I diabetes, the patient's glucose level is controlled, typically through diet and insulin. However, the present method utilizes treatment with choline in order to control the patient's lipid profile, and particularly the patient's free fatty acids levels.

Choline is a water-soluble essential nutrient, which is usually grouped within the B-complex vitamins. Choline generally refers to the various quaternary ammonium salts containing the N,N,N-trimethylethanolammonium cation. These naturally occurring ammonium salts are found in the lipids that make up cell membranes, and in the neurotransmitter acetylcholine. Specifically, choline is a quaternary saturated amine with the chemical formula $(CH_3)_3N^+CH_2CH_2OHX^-$, where X— is a counterion, such as chloride, hydroxide or tartrate.

In humans, choline and its metabolites are needed for three main physiological purposes: structural integrity and signaling roles for cell membranes; cholinergic neurotransmission (acetylcholine synthesis); and as a major source for methyl groups via its metabolite, trimethylglycine (betaine), which participates in the S-adenosylmethionine synthesis pathways.

The present treatment method includes the step of administering to the patient a therapeutically effective dosage of choline or a pharmaceutically acceptable salt thereof. In human patients, the effective dosage of choline is preferably approximately 10 mg., delivered daily. Although the choline may be injected in solution, it is preferably delivered orally to the patient.

The use of choline as an effective treatment for type I diabetes has been shown experimentally by the inventor. Type I diabetes mellitus was induced chemically in experimental rats by an intraperitoneal (IP) injection of 55 mg/kg body weight streptozotocin (STZ) freshly dissolved in 5 mmol/L citrate buffer, with a pH of 4.5.

For all groups, blood was tested for basal glucose, before induction of diabetes for basal glucose determination, after the second day, and after the first and second weeks of induction of diabetes. Four groups of rats (with a total of forty rats, with ten rats per group) were studied: group C (the control group), group D (diabetic, but untreated), group C/Ch (control group treated with choline), and group D/Ch (diabetic and treated with choline) for two weeks.

Figure 1:
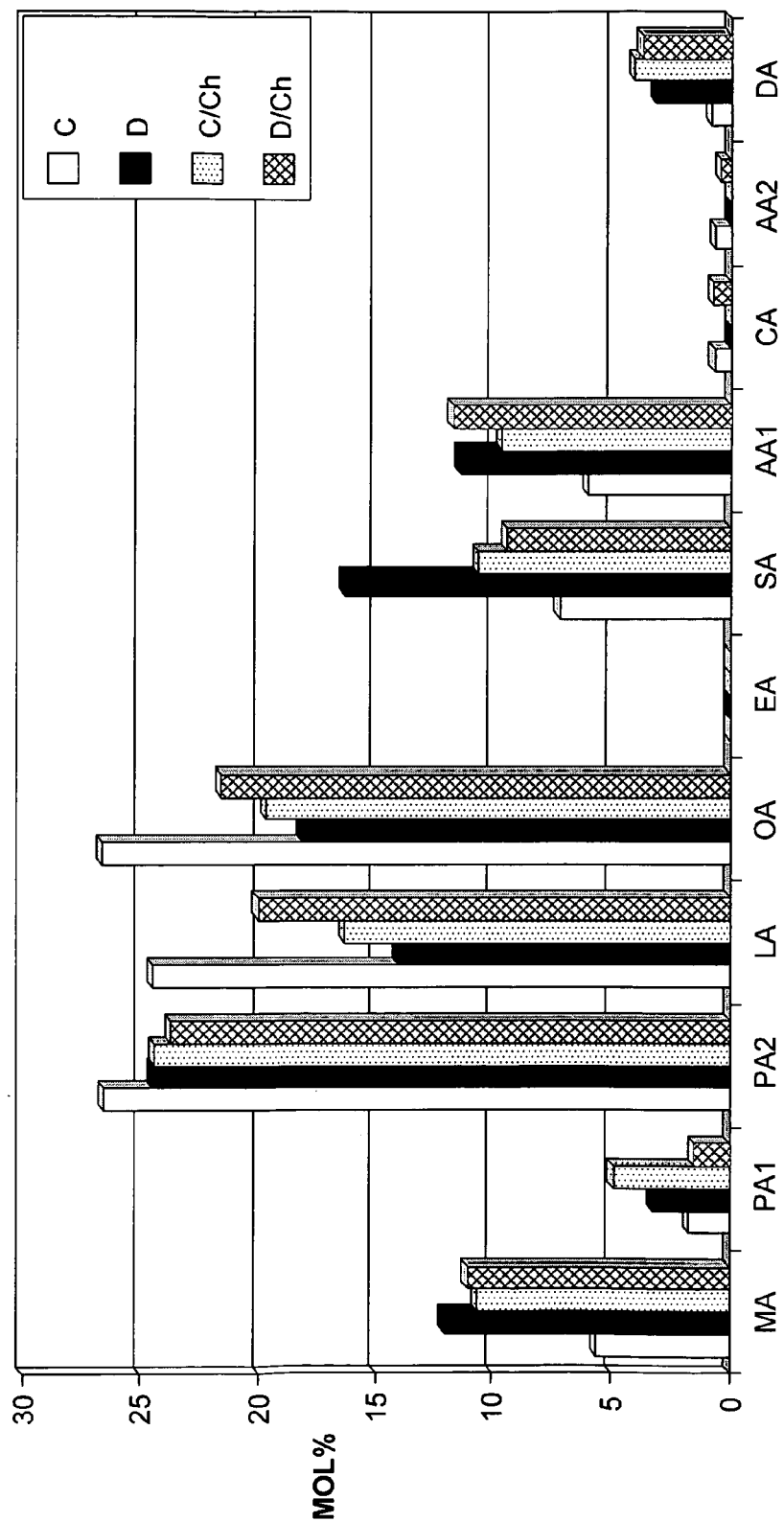
FIG. 1 is a graph illustrating molar concentrations of differing un-esterified fatty acids in four groups of experimental rats, including a control group of rats, a diabetic group of rats, a group of rats without diabetes and dosed with choline according to the method of the present invention, and a group of rats with diabetes and dosed with choline according to the method of the present invention.
Figure 2:
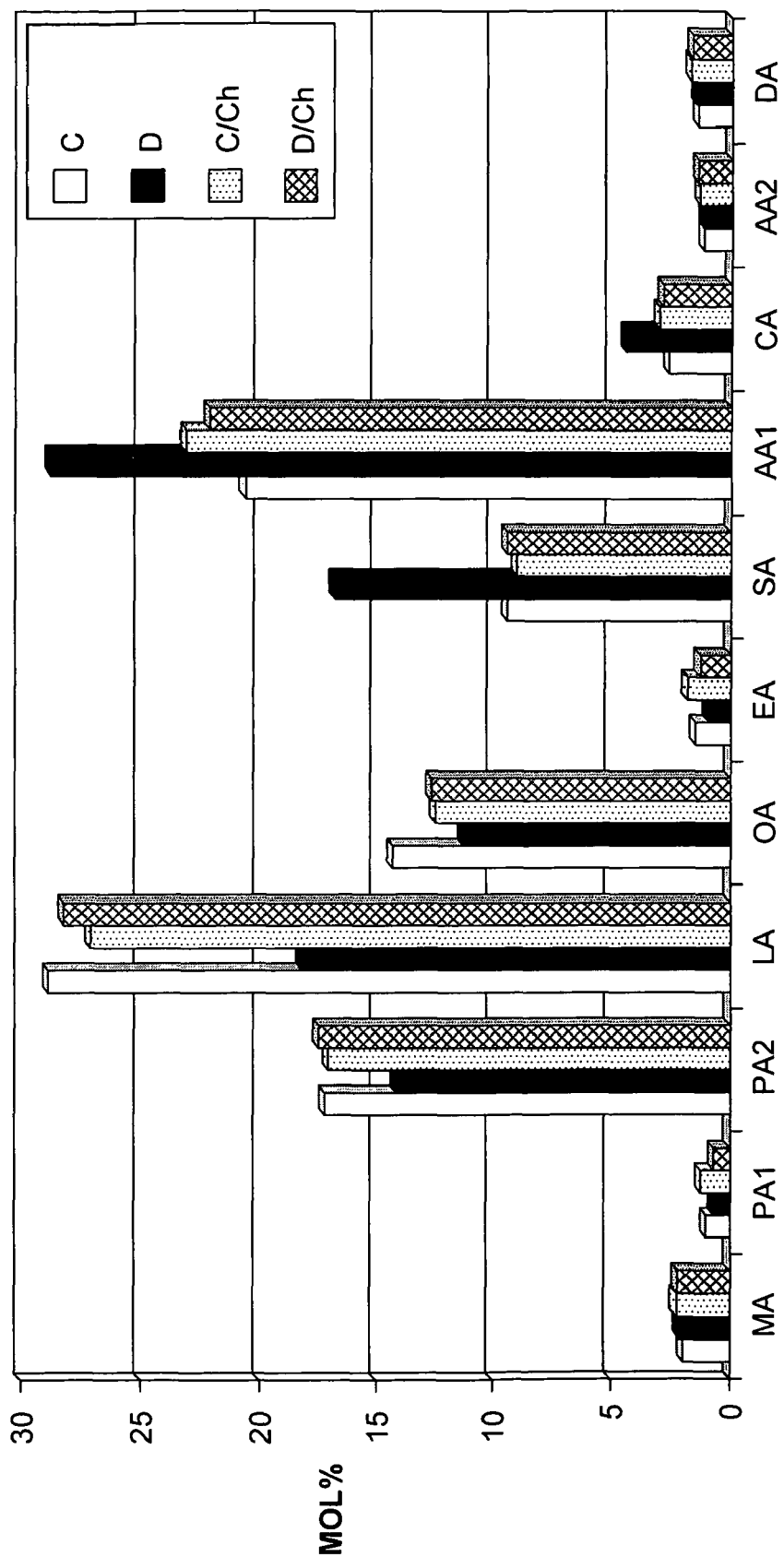
FIG. 2 is a graph illustrating molar concentrations of differing total fatty acids in the four groups of experimental rats of FIG. 1.

FIG. 1 represents the molar concentrations of un-esterified fatty acids in group C, group D, group C/Ch and group D/Ch after the two week treatment period, and FIG. 2 illustrates the molar concentrations of total fatty acids, also for the four experimental groups. In FIGS. 1 and 2, each set of results for all four groups are shown for specific fatty acids. The first set of results represents the molar concentrations of myristic acid (MA); the second set of results represent the molar concentrations of palmitoleic acid (PA1); the third set of results represent the molar concentrations of palmitic acid (PA2); the fourth set of results represent the molar concentrations of linoleic acid (LA); the fifth set of results represent the molar concentrations of oleic acid (OA); the sixth set of results represent the molar concentrations of elaidic acid (EA); the seventh set of results represent the molar concentrations of stearic acid (SA); the eighth set of results represent the molar concentrations of arachidonic acid (AA1); the ninth set of results represent the molar concentrations of cervonic acid (CA); the tenth set of results represent the molar concentrations of adrenic acid (AA2); and the eleventh set of results represent the molar concentrations of docosapentaenoic acid (DA).

The results of the testing over the four groups, illustrated in FIGS. 1 and 2, show that diabetes may result from an imbalance or lack of choline in the body. In a healthy body, cells utilize extracellular choline, which is passed through the blood and metabolized from food. Choline is a dietary component that is important for the health and construction of structural components of cell membranes, as well as the processes involved in cell signaling, cholinergic neurotransmission, and lipid (i.e., fat) transport and metabolism.

In the liver, fat and cholesterol are packed into lipoproteins, known as very low-density lipoproteins (VLDL), for transport through the blood to tissues. Choline-containing phospholipid, such as phosphatidylcholine (i.e., lecithin or PtdCho), is a requisite component of VLDL particles, and without adequate PtdCho, fat and cholesterol accumulate in the liver, thus preventing the infiltration of fat into the liver and preventing the subsequent liver damage.

The experimental results illustrated in FIGS. 1 and 2 show that a daily oral dose of choline allows for the control of diabetes lipid metabolism, thus preventing diabetes-induced complications. Administration of choline to diabetic rats has been shown to improve many fatty acid levels back to initial control levels, thus representing a prevention of diabetic-related liver damage. The daily dosing of choline regulates (and also prevents) fatty acid accumulation in the liver, which often causes functional damage to the liver in diabetes patients.

It is to be understood that the present invention is not limited to the embodiment described above, but encompasses any and all embodiments within the scope of the following claims.

I claim:

1. A method of treating type I diabetes, comprising the step of administering to a patient a therapeutically effective dosage of choline or pharmaceutically acceptable salts thereof for the treatment of type I diabetes, wherein the choline is delivered to the patient in a daily dosage of 10 mg.

2. The method of treating type I diabetes as recited in claim 1, wherein the step of administering to the patient the therapeutically effective dosage of choline includes delivery of the choline to the patient through oral delivery.

* * * * *